United States Patent
Stisen

(10) Patent No.: US 6,582,379 B1
(45) Date of Patent: Jun. 24, 2003

(54) APPARATUS AND METHOD OF MEASURING THE FLOW OF A LIQUID, IN PARTICULAR URINE, FROM A PATIENT

(75) Inventor: Børge Stisen, Græsted (DK)

(73) Assignee: Maersk Medical A/S, Hundested (DK)

( * ) Notice: Subject to any disclaimer, the term of this patent is extended or adjusted under 35 U.S.C. 154(b) by 0 days.

(21) Appl. No.: 09/719,344
(22) PCT Filed: Sep. 24, 1999
(86) PCT No.: PCT/DK99/00502
§ 371 (c)(1), (2), (4) Date: Dec. 8, 2000
(87) PCT Pub. No.: WO00/18298
PCT Pub. Date: Apr. 6, 2000

(30) Foreign Application Priority Data

Sep. 25, 1998 (DK) .......................... 1998 01214

(51) Int. Cl.$^7$ .............. G01F 1/66; G01F 15/00; G01F 17/00; G01F 23/28; B65D 81/00; A61M 1/00
(52) U.S. Cl. ............. 600/573; 600/580; 600/582; 604/318; 604/322; 73/290 V; 73/861.27; 73/149
(58) Field of Search ................. 600/573, 580, 600/582; 604/318, 322; 73/290 V, 861.27, 149

(56) References Cited

U.S. PATENT DOCUMENTS

| | | |
|---|---|---|
| 3,241,368 A | 3/1966 | Newitt |
| 4,229,798 A * | 10/1980 | Rosie et al. ............. 340/621 |
| 4,448,207 A | 5/1984 | Parrish |
| 4,535,627 A | 8/1985 | Prost et al. |
| 4,599,892 A | 7/1986 | Doshi |
| 4,658,834 A | 4/1987 | Blankenship et al. |
| 4,683,748 A | 8/1987 | Carter |
| 4,811,595 A | 3/1989 | Marciniak et al. |
| 4,939,457 A * | 7/1990 | Tellerman .............. 324/207.13 |
| 4,972,844 A * | 11/1990 | Cianci et al. ............... 600/573 |
| 4,991,433 A | 2/1991 | Warnaka et al. |
| 5,251,482 A | 10/1993 | Bates et al. |
| 5,263,370 A * | 11/1993 | Murata et al. .............. 600/584 |
| 5,533,389 A | 7/1996 | Kamen et al. |

(List continued on next page.)

FOREIGN PATENT DOCUMENTS

| | | |
|---|---|---|
| DE | 155872 A | 7/1982 |
| EP | 0 462 342 A1 | 12/1991 |
| EP | 0 416 267 B1 | 4/1994 |
| GB | 1 440 185 | 6/1976 |
| GB | 1 462 949 | 1/1977 |
| JP | 9015020 A | 1/1997 |
| WO | WO 87/01025 | 2/1987 |

OTHER PUBLICATIONS

English Language Abstract Of JP950152376—Liquid Quantity Detect Tank Control Helmholtz Resonance Principle Computation Amount Liquid Tank Based Frequency Sound Wave Emit Loudspeaker Maximum Level Sound Set.

Primary Examiner—Henry Bennett
Assistant Examiner—Kathryn Ferko
(74) Attorney, Agent, or Firm—Brinks Hofer Gilson & Lione

(57) ABSTRACT

An apparatus for measuring the discharge of a liquid, in particular urine, from a patient. The apparatus includes a measuring container (1), means (H) for applying a first acoustic signal to the liquid-empty part of the measuring container (1), means (H) for recording a second acoustic signal generated in the measuring container (1) in response to the first signal, means (45) for determining a current liquid amount in the measuring container (1) on the basis of the second acoustic signal. The measuring container (1) has a measuring pipe (5) defining a liquid-empty resonance chamber for generating the second acoustic signal.

14 Claims, 5 Drawing Sheets

Figure 1:
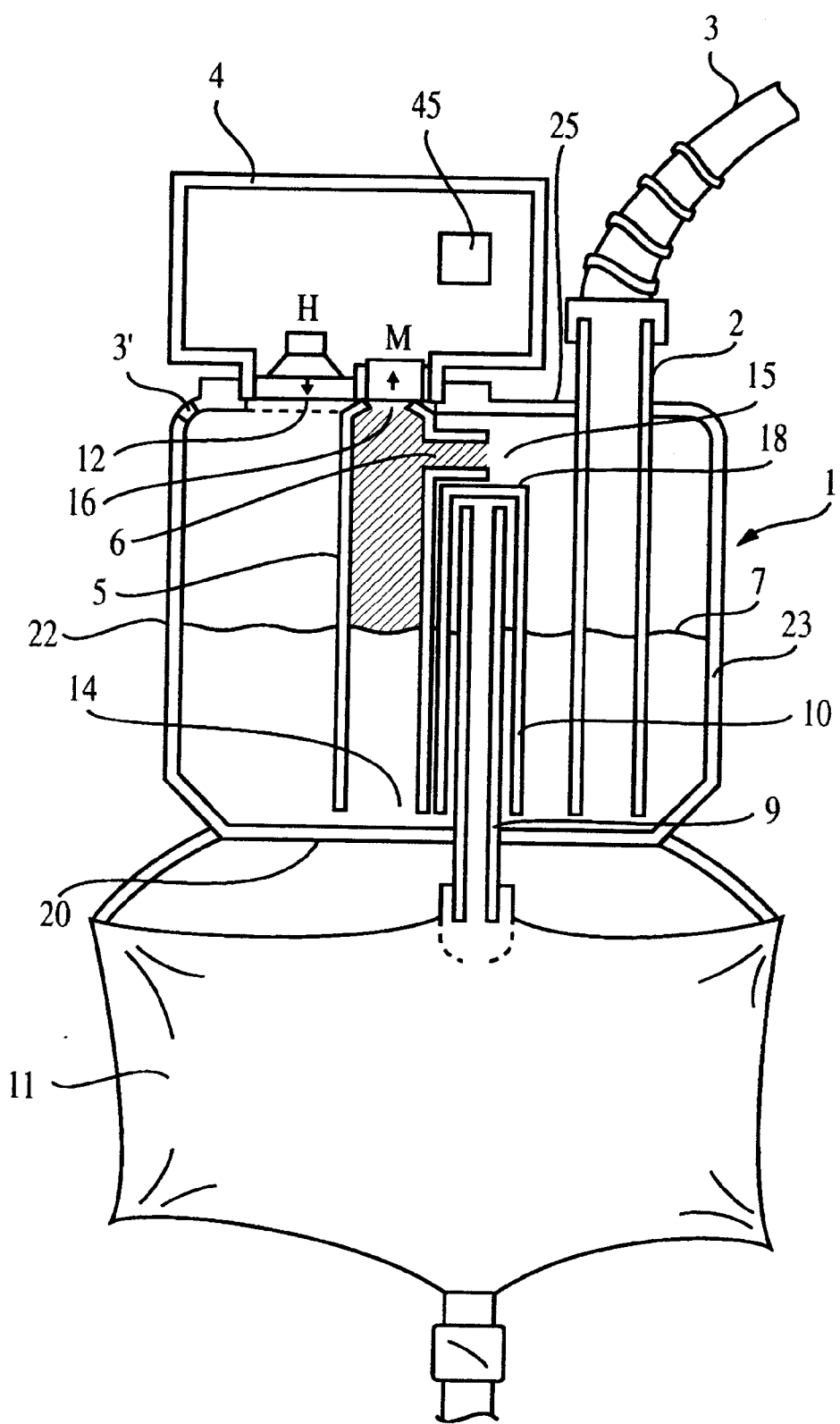

U.S. PATENT DOCUMENTS 5,533,402 A    7/1996  Sarvazyan et al.
5,586,085 A  * 12/1996  Lichte ........................ 367/165
5,741,238 A  *  4/1998  Bradbury et al. ............ 604/322
6,178,827 B1 *  1/2001  Feller ...................... 73/861.22

* cited by examiner

APPARATUS AND METHOD OF MEASURING THE FLOW OF A LIQUID, IN PARTICULAR URINE, FROM A PATIENT

The present invention relates to an apparatus for measuring the flow of a liquid, in particular urine, from a patient. More particularly, the invention relates to an apparatus of the type which comprises a measuring container having a bottom wall, a top wall and side walls and having an inlet opening for the liquid and adapted to define a state of maximum filling in which a liquid-empty part of the container has a smallest volume, and which also comprises means for emitting a first acoustic signal to the liquid-empty part of the measuring container, means for recording a second acoustic signal generated in the measuring container in response to the first signal, and means for determining a current amount of liquid in the measuring container on the basis of the second acoustic signal.

The invention also relates to a method of measuring the flow of a liquid, in particular urine, from a patient. The method uses an apparatus comprising a measuring container having a bottom wall, a top wall and side walls and having an inlet opening for the liquid and adapted to define a state of maximum filling in which a liquid-empty part of the container has a smallest volume, and which also comprises means for emitting a first acoustic signal to the liquid-empty part of the measuring container, means for recording a second acoustic signal generated in the measuring container in response to the first signal, and data processing electronics for determining a current amount of liquid in the measuring container via activatable connecting means, and which has a larger volume relative to the measuring container, said connecting means being adapted to allow draining of the measuring container in the state of maximum filling.

U.S. Pat. No. 4,658,834, e.g., already discloses an apparatus of this type. However, it is a common feature of the known apparatuses that they are relatively large, and that they moreover require a specially constructed apparatus housing to ensure correct operation of the apparatus. These inexpediencies as well as other problems are remedied according to the invention in that the measuring container has a measuring pipe having a first opening, a second opening and a third opening, said first opening being arranged to allow flow of the liquid into the measuring pipe to define a liquid surface in the measuring pipe, said second opening being arranged so as to communicate with the part of the measuring container empty of liquid at any time, said third opening being arranged so as to communicate with the means for recording the second acoustic signal, said second and third openings together with the surface of the liquid in the measuring pipe defining a liquid-empty resonance chamber to generate the second acoustic signal. By means of this apparatus, measuring may be performed in a quite particularly advantageous manner by using the so-called Helmholz resonator principle, and the apparatus is also unique e.g. by being more compact than other apparatuses which utilizes this principle.

By moreover providing the apparatus with an automatically operating draining mechanism which causes automatic draining of the measuring container under given circumstances, it is possible to manufacture an even more compact measuring container, which requires a very small volume for measurements to be performed. The draining mechanism may particularly advantageously be constructed wherein the connecting means comprise an automatically operating syphon mechanism adapted to provide draining of the measuring container in the maximum filling state, which provides an especially low cost solution.

The apparatus makes it possible to manufacture the measuring container with an optimum compactness, with the measuring pipe fully integrated in the measuring container. The apparatus also makes it possible to provide a solution in which the bacteriologically contaminated parts may be kept separated from the signal generating and receiving means as well as from the determining means, thereby allowing a distinction to be made between reusable components and disposable components.

When the measuring container is provided with the temperature correcting pipe utilizing the Helmholz Resonance principle, it is possible in a quite advantageous manner to compensate for temperature variations of the liquid which may otherwise give rise to incorrect measurements under certain circumstances.

The temperature correcting pipe is filled with a gas, which is preferably air.

The invention also relates to an advantageous method for providing accurate measurements in apparatuses which utilize the Helmholz resonator principle, and in which the measuring container is drained regularly, there being performed an estimation of the admission to the measuring container during the actual draining. A particularly expedient estimate may be performed wherein the estimate V is determined as $V=(T*A_{top}+T*B_{bottom})/2$, where, T represents the duration of the draining.

Figure 2:
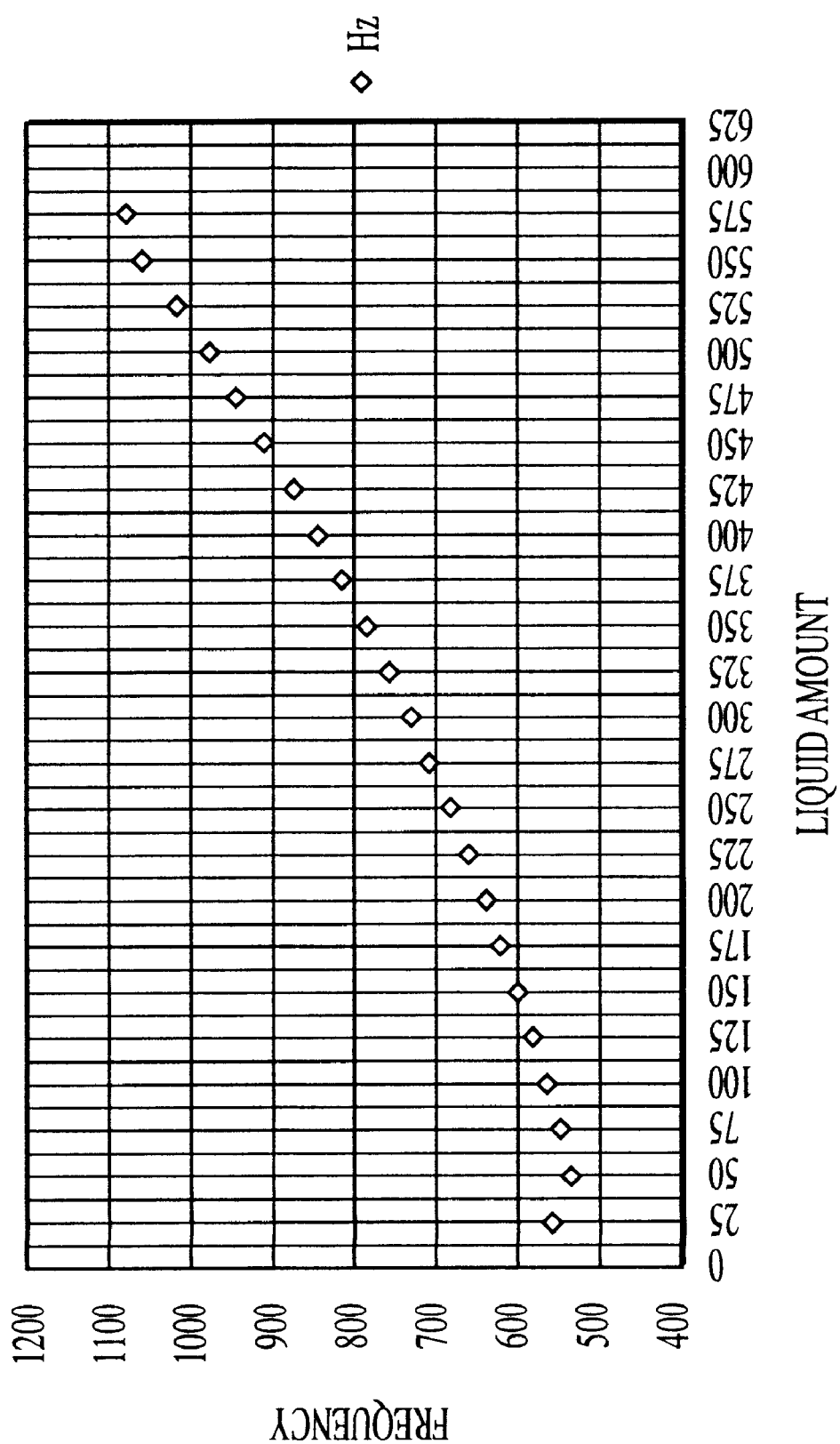
Figure 3:
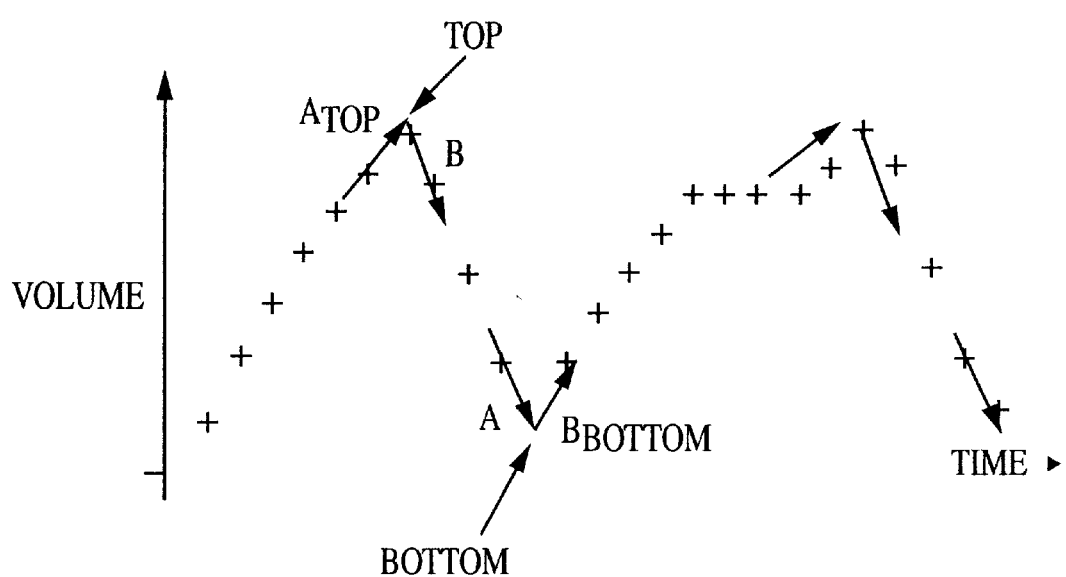
Figure 4:
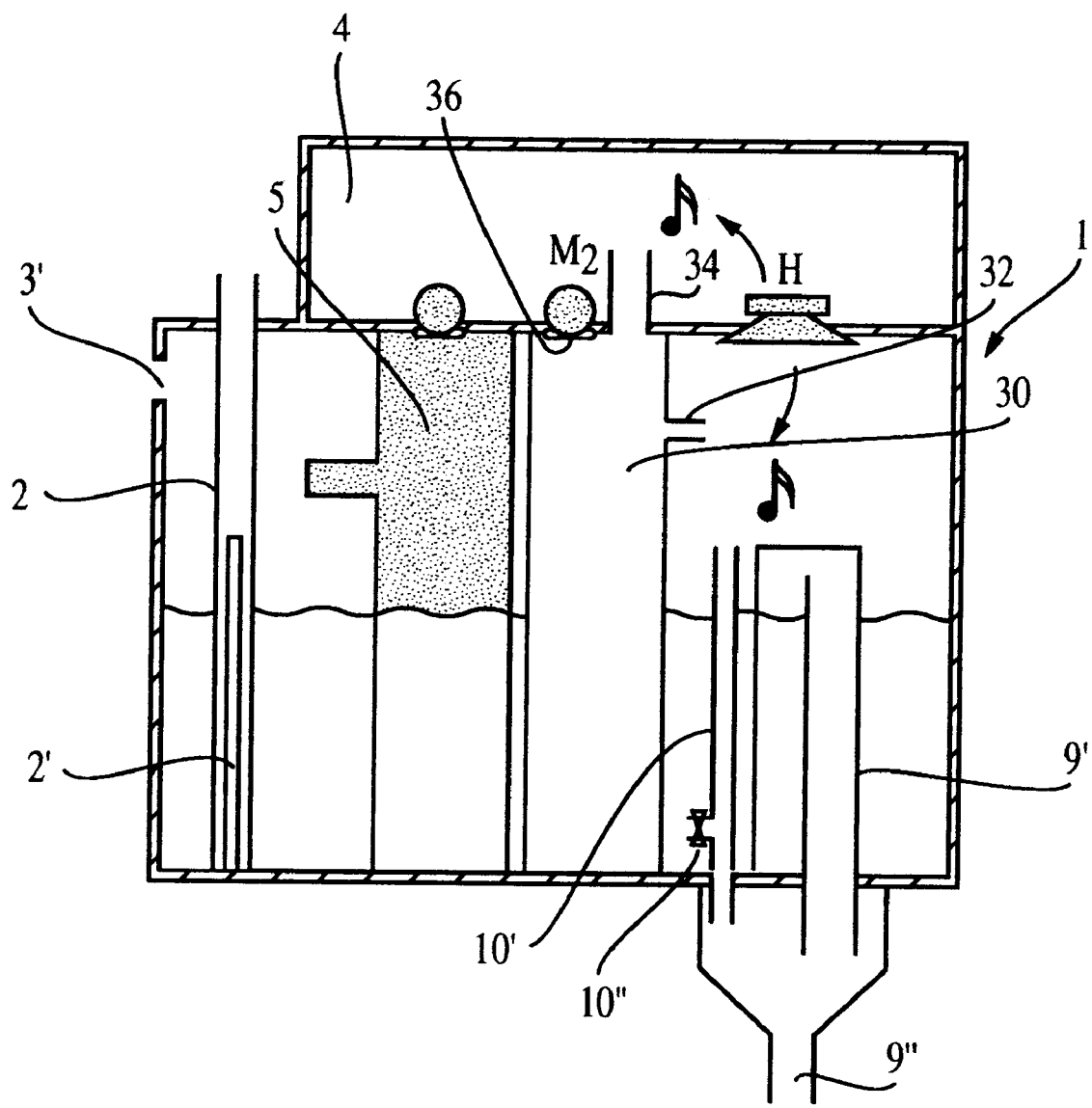
Figure 5:
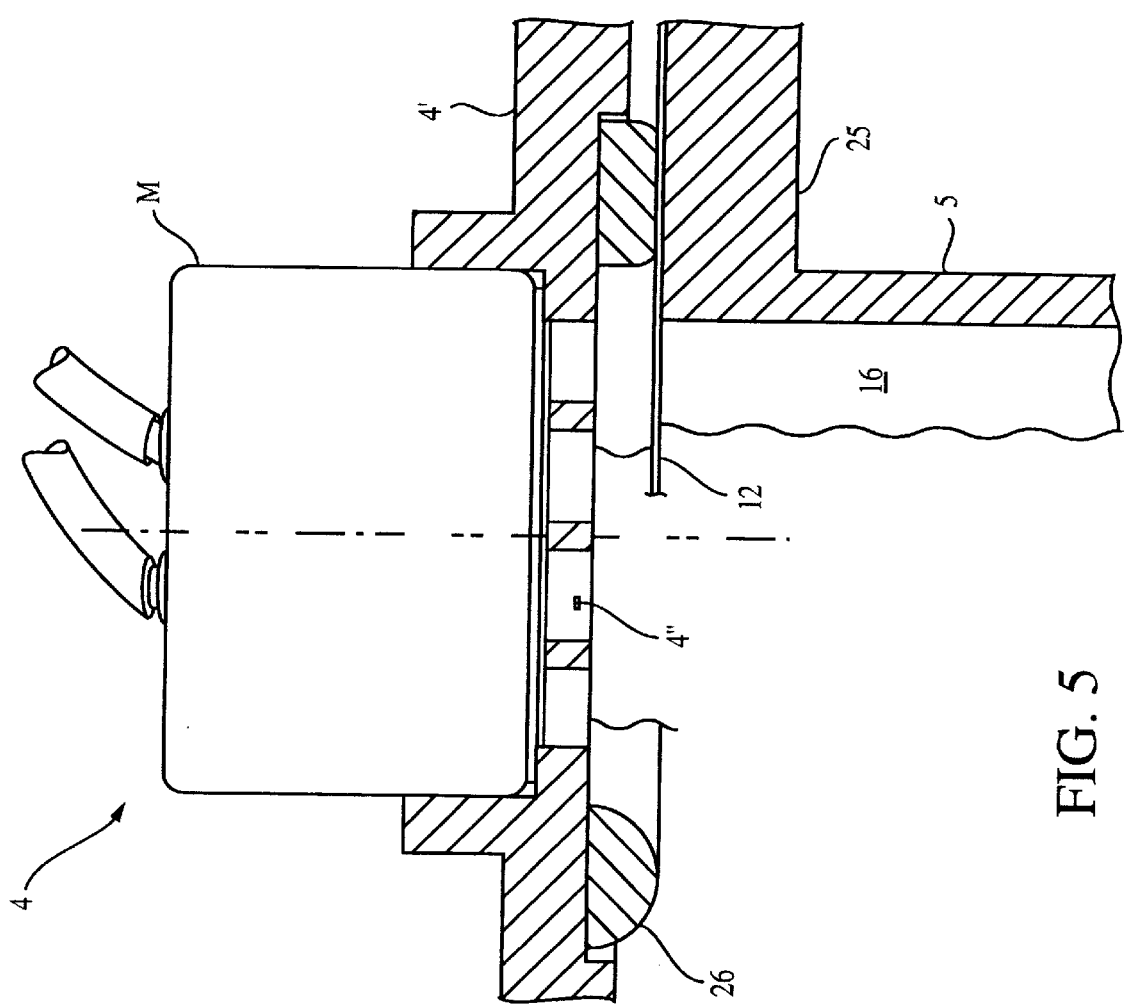

The invention will be described more fully below with reference to an embodiment shown in the drawing. In the drawing:

FIG. 1 shows a cross-section through an apparatus according to the invention,

FIG. 2 shows an example of the variation of the resonance frequency in dependence on the liquid amount expressed as a height level in the measuring container, FIG. 3 shows a method of estimating the admission to the measuring container during draining, FIG. 4 shows the apparatus shown in FIG. 1 in a modified version with a temperature compensating device, and FIG. 5 shows an enlarged section of the connecting area between the measuring container and the measuring housing.

The apparatus shown in FIG. 1 for measuring the discharge of urine from a patient comprises a measuring container 1 to which urine is supplied via an inlet opening 2 and a hose 3 from the patient. The hose 3 may form part of a catheter inserted into the patient, so that the said supply can typically take place approximately continuously over a period. The measuring container is intended to be mounted on e.g. a hospital bed by means of brackets (not shown), said measuring container being oriented as shown in the drawing in the correctly mounted position. The measuring container is moreover connected with a urine collecting container 11. It will be appreciated that the measuring container 1 and the collecting container 11 are typically disposable parts, as these two parts are discarded when the measurement of the flow from the patient ceases. The side wall 22 of the measuring container 1 has a small opening 3' to the atmosphere to allow pressure equalization.

The inlet opening 2 terminates at a bottom wall 20 in the measuring container 1, and the measuring container 1 is moreover defined by side walls 22, 23 so that the measuring container 1 preferably has an approximately quadrangular cross-section. In addition, the measuring container 1 is defined upwardly by a top wall 25 having an opening covered by a liquid-and-air-tight sheet 12, thereby insuring i.e. a reliable, bacteriologically tight boundary between the soiled side and the clean side of the apparatus in the use of the apparatus, as will appear from the following.

A separate measuring housing 4 is arranged against the outer side of the measuring container 1 and in connection with the sheet 12, said separate measuring housing being firmly, but releaseably connected with the measuring container 1 by engagement means not shown. The measuring housing 4 forms part of the clean side of the apparatus, the sheet 12 separating the measuring housing 4 from the contents of the measuring container 1, and the measuring housing 4 may therefore be used repeatedly. The measuring housing 4 comprises measuring equipment in the form of a loud speaker (H), a microphone (M), control and data processing electronics (microprocessor) 45 with a memory as well as a display visible from the outside and a power supply which may preferably be formed by a battery. The loud speaker (H) is adapted and arranged to emit an acoustic signal which is transferred via the sheet 12 to the interior of the measuring container 1, and the microphone is adapted and arranged to record an acoustic signal which is generated in a defined area in the measuring container 1 in response to the signal from the loud speaker. In the correctly mounted state, the microphone and the loudspeaker preferably engage the sheet relatively tightly, and it will be appreciated that the sheet should preferably be relatively thin and soft so that it has no noticeable importance and for the acoustic properties of the apparatus. Further, the measuring housing 4 may preferably comprise keys by means of which a user of the apparatus, typically the hospital nursing staff, may at any time request determination of the liquid admission to the measuring container 1 within a selected period of time, which may e.g. be the last 15 or 30 minutes, on the basis of the data stored in the memory of data processing electronics 45, and these values may then be displayed on the display.

The interior of the measuring container 1 accommodates an elongated measuring pipe 5 having a longitudinal axis which, in the correctly mounted position of the apparatus, preferably extends approximately perpendicularly to the surface 7 of the liquid in the container 1, and which has a first opening 14 arranged immediately above the bottom wall 20 of the measuring container. The pipe 5 additionally has a lateral branch 6 arranged at the end of the pipe 5 opposite the bottom wall 20, and the pipe 5 terminates here in a second, further opening 15. Moreover, a third opening 16 for the pipe 5 is provided opposite the first opening 14, and this third opening is positioned so as to be aligned with the microphone M when the measuring housing 4 is secured to the measuring container 1. In this position, the opening 16 preferably intimately engages the sheet 12 in order to avoid interfering noise. In the embodiment shown, the part of the measuring pipe 5 extending between the openings 14 and 16 is cylindrical, but in principle the measuring pipe may have any shape, the essential point being that the pipe has the mentioned openings. Although the element 5 is disclosed herein as being formed as a cylindrical pipe, any suitable geometry, such as elements having a non-circular cross-section, may be used as long as the overall objective of the invention is fulfilled.

To limit the dimensions and thereby the manufacturing cost of the measuring container 1 with the pipe 5, the measuring container 1 moreover comprises a system by means of which the measuring container 1 may be drained periodically and automatically. The draining system or draining mechanism may preferably comprise a pipe 9 which is open upwardly, and a further pipe 10 which is arranged to enclose the pipe 9, and which is open downwardly and closed upwardly with its end 18. The end 18 of the pipe 10 is preferably spaced below the lateral branch 6 of the measuring pipe 5. It will be appreciated that the draining system operates as a syphon, and that the measuring container 1 is drained when the level of the liquid surface 7 in the measuring container 1 increases the open end of the inner pipe 9. During draining, the liquid in the measuring container 1 is conveyed through the inner pipe and into the collecting container 11, which may be a conventional detachable/replaceable type, and which may be adapted to collect the amount of urine which is discharged by a patient during e.g. 24 hours. The draining continues until air flows from the measuring container inwards between the inner pipe 9 and the outer pipe 10. It will thus be appreciated that the discharged urine merely flows through the measuring container, and that the dimensions of the measuring container may hereby be limited to a minimum in accordance with the measuring principle described more fully below. The described, automatically operating draining system is not absolutely necessary for the use of the apparatus, since, alternatively, a manual valve may be provided by means of which the nursing staff may cause the contents of the measuring container 1 to flow into the collecting container 11. It will be clear, however, that such a solution is relatively inexpedient in view of the fact that the draining is to be carried out at short intervals.

The apparatus operates in the following manner. Urine flows into the measuring container 1 via the hose 3 between two successive drainings of the measuring container and also during the actual draining, whereby the level of liquid surface 7 in the measuring container 1 increases. The liquid also flows into the pipe 5 so that the height of the liquid in the measuring pipe 5 corresponds to the height of the liquid surface 7 outside the measuring pipe in the measuring container 1. The measuring pipe 5, together with pipes 9 and 10, may preferably be arranged centrally in the measuring container by means of retention ribs connected with the walls or the top wall of the measuring container 1, so that the liquid level in the pipe 5 will be less sensitive to a possibly incorrect oblique position of the measuring container 1 on e.g. a hospital bed. In the area between the liquid surface in the pipe 5 and the third pipe opening 16 opposite the bottom wall, there is an air-filled area having a well-defined volume, which is shown hatched in FIG. 1, and this volume decreases gradually during the flow of the liquid into the measuring container 1, i.e. when the liquid level increases in the pipe 5. It will be appreciated that changes in this volume may serve as a measure of the flow into the measuring container, and the flow into the measuring container is thus measured according to the invention by currently recording values of this volume.

More particularly, this recording takes place by utilizing the principles of a Helmholz resonator, with the resonance frequency of the measuring pipe 5 depending on the volume of the air-filled area in the measuring pipe 5. By determining the resonance frequency at a given time, it is thus possible, on the basis of a calibration of the data processing electronics, to determine the current liquid height in the measuring pipe 5 and thereby the inflow of liquid in a given period of time $(t_1-t_2)$ by comparing liquid height recordings for $t_1$ and $t_2$, respectively. The measuring pipe 5 is excited to the resonance frequency of the loudspeaker H, which emits a short acoustic signal at given time intervals which varies, i.e. sweeps, within a predetermined frequency interval. The predetermined frequency interval may be determined so as to be between the resonance frequency of the measuring pipe 5 in the empty state and the filled state, respectively, i.e. immediately after and before the draining of the measuring container 1. It should be noted that the dimensions of the measuring container should be selected such that the loudspeaker just gives rise to resonance in the measuring pipe 5 during this interval.

As mentioned initially, the loudspeaker H is arranged in the measuring housing 4, and it will be appreciated that the loudspeaker emits the acoustic signal through the cover sheet 12 and into the liquid-empty part of the measuring container above the surface 7. From there, the signal propagates to the lateral branch 6 of the pipe 5, whereby the resonance frequency of the pipe 5 is excited via the lateral branch 6 when the loudspeaker frequency corresponds exactly to the resonance frequency. Thus a further or second acoustic signal is generated in response to the loudspeaker signal. It should be mentioned again that the opening 16 is preferably very closely engaged with the sheet 12 to avoid interfering noise. To reduce the consumption of energy and thereby increase the service life of the mentioned battery, the limits of the sweep range may optionally be determined to vary within limited empirical values recorded in the data processing electronics 45, and these values may e.g. depend on a preceding recorded value of the current liquid height in the measuring pipe 5.

The measuring housing 4, as likewise mentioned, comprises a microphone M arranged immediately at the third opening 16 of the measuring pipe 5 above the sheet 12, and this microphone M records sound signals generated in measuring pipe 5. When the resonance frequency of the pipe 5 is excited, the signal received by the microphone will change characteristic, and at this time the data processing electronics 45 record the resonance frequency of the pipe 5 and convert the frequency value in question into an expression of a liquid height. Optionally, the flow to the container since the last recording may be calculated already at this time. It will be appreciated that the performed calculations are performed on the basis of calibration data stored in the memory of data processing electronics 45, so that the prescribed conversion into liquid height values may be carried out. A typical relation is shown in FIG. 2.

As the dimensions of the measuring container 1 are preferably to be relatively small, the measuring container will be drained at short intervals in the use of the apparatus. The measuring container may thus have dimensions of about 75×75×30 cm corresponding to a volume of about 175 ml, and the draining mechanism may be adapted to cause draining of the container when this is filled 75%. With a time diuresis that may constitute up to 500 ml, this will give rise to up to about 4 drainings per hour. As the performance of the apparatus must be ensured at any time during use, i.e. independently of whether a draining has been effected within a predetermined period $(t_1-t_2)$ of e.g. 1–5 minutes, it is also necessary to be able to allow for the amount of liquid V which has flown into the measuring container 1 during the draining that may have a duration T of 5–10 seconds. This takes place as shown in FIG. 3 by making an estimate of the admission on the basis of first data for the change in the liquid amount in the container immediately before the draining and second data for the change of the liquid amount in the container immediately after the draining. By determining the average of these two values and multiplying the average with the duration T of the draining, the estimate for V may be determined. In FIG. 3, the liquid amount in the measuring container 1 is shown as a function of time, and $A_{top}$ and $B_{bottom}$, respectively, indicate curve gradients which may preferably constitute the first data and the second data, respectively. The processing electronics may be programmed to determine these gradients when the liquid level in the pipe 5 assumes a given value, i.e. on the basis of measurements performed at times $t_{1A}$, $t_{2A}$ and $t_{1B}$, $t_{2B}$ which correspond to liquid levels in the pipe 5 immediately before and after the draining.

As the resonance frequency of the measuring pipe depends on the velocity of sound in the air, and as this velocity depends on the temperature of the air, it may be expedient to allow for temperature variations caused by the temperature of the inflowing liquid that give rise to a general heating of the measuring container, in order to achieve improved accuracy of the apparatus. According to the invention, these temperature variations may be compensated, as shown in FIG. 4, by incorporating a further resonator pipe 30 which may selectively be excited for resonance via a lateral branch with an opening 32 or via a branch with an opening 34 protruding into the measuring housing 4. The resonator pipe 30 is closed downwardly and preferably extends right down to the bottom wall of the measuring container 1 with its lower end. However, if desired, the lower end of the pipe 30 may be arranged in the part of the measuring container 1 which is empty of liquid at any time. It will be appreciated that in practice it is decided to construct the pipe 30 with just one of the lateral branches according to the use. Thus, in certain situations it may be less expedient to use a lateral branch 32 which terminates in the measuring container 1, as possible shakings of the apparatus may cause unintentional flow of liquid into the pipe 30. The resonator pipe 30 additionally has a further opening 36 which faces toward a microphone $M_2$. In principle, the structure shown in FIG. 4 may comprise the same subcomponents as the apparatus shown in FIG. 1, including a sheet diaphragm that may form a seal between the measuring housing 4 and the measuring container 1, and with which the microphone $M_2$ is engaged.

In the use of the system shown in FIG. 4, the air in the resonator pipe 30 is heated to a temperature corresponding to the temperature of the liquid because of heat conduction between the liquid and the wall of the pipe 30 and possibly (if the lateral branch 32 is used) directly from the liquid surface by convection. Since the resonator pipe 30 has a fixed length and thereby a well defined volume, this pipe will likewise be excited for resonance by the acoustic signal from the loud speaker, and this resonance frequency will solely depend on the velocity of the air in the pipe 30, which in turn depends on the air temperature in the pipe 30. The microphone $M_2$ associated with the pipe 30 is used, quite as described for the measuring pipe 5, together with the data processing electronics 45, for determining a resonance frequency for the pipe 30, and the measured resonance frequency will be an expression of the prevailing temperature of the liquid. By means of data stored in the memory of data processing electronics 45, it will then be possible to correct the recorded values of the liquid height in the pipe 5 in accordance with the measured temperature.

The measuring container shown in FIG. 4 is characterized by an alternative structure of the urine supply inlet opening 2. The inlet opening 2 is here formed with a filter which, as shown, is preferably shaped in a simple manner as an elongated slot-shaped outlet 2' dimensioned such that possible content of coagulated blood in the urine, which might give rise to clogging of the draining mechanism, is retained in the supply inlet opening 2. In the embodiment shown, the draining mechanism comprises an overflow pipe 10' with a lateral branch capable of allowing draining of the container at any time via an externally operated valve 10". A one-way valve 9" arranged at the outlet of the draining mechanism in the collecting container 11 (not shown) prevents back flow of urine, e.g. if, by mistake, the apparatus is moved from the normal upstanding position.

FIG. 5 shows an enlarged section of the connection between the measuring container 1 and the measuring housing 4 in the area at the microphone M and the measuring pipe 5 which, as shown in this embodiment, is formed integrally with the top wall 25 of the measuring container 1. The bottom wall 4' of the measuring housing 4 comprises respective openings for the microphone M, M₂ and the loudspeaker H, one such opening 4" being shown in the figure below the microphone M and above the third opening 16 of the measuring pipe. A peripheral sealing ring 26 of e.g. foamed plastics extends around the opening 4" which, as shown, may optionally be protected by ribs, and serves to form a tight connection between the microphone M and the measuring pipe 5. The figure also shows the diaphragm formed by the sheet 12 which forms the upper termination of the measuring container 1.

What is claimed is:

1. An apparatus for measuring the discharge of a liquid, in particular urine, from a patient, and comprising:
    a container (1) for receiving said liquid, said container (1) having a bottom wall (20), a top wall (25), side walls (22, 23) and an inlet opening (2) for said liquid,
    said container (1) being adapted to define a state of maximum filling in which a liquid-empty part of the container (1) has a smallest volume,
    a measuring pipe (5) having a first opening (14), a second opening (15) and a third opening (16),
    said first opening (14) communicating with said container (1) such that said liquid in said container (1) defines a surface (7) of said liquid within said measuring pipe (5), said surface (7) being at a highest level in said state of maximum filling of said container (1),
    said second opening (15) being arranged so as to communicate with said liquid-empty part of said container (1),
    means (H) for emitting a first acoustic signal through said liquid-empty part of said container (1),
    said second (15) and third (16) openings together with said liquid surface (7) in said measuring pipe (5) defining a liquid-empty resonance chamber,
    means (M) communicating with said third opening (16) for recording a second acoustic signal generated in said resonance chamber in response to said first signal, and
    means (45) for determining a current amount of liquid in said measuring container (1) on the basis of said second acoustic signal recorded by said means (M) for recording.

2. A apparatus according to claim 1, further comprising a collecting container (11) which is in flow communication with the measuring container (1) via activatable connecting means (9, 10), and which has a larger volume relative to the measuring container (1).

3. An apparatus according to claim 2, wherein the connecting means further comprise an automatically operating syphon mechanism (9, 10) adapted to provide draining of the measuring container (1) in said state of maximum filling.

4. An apparatus according to claim 1, wherein the measuring pipe (5) further comprises a cylindrical first part extending substantially vertically in the correctly mounted position and arranged in the measuring container (1) to extend upwards from the bottom wall (20) of the container, and a substantially cylindrical lateral branch (6) whose one end terminates in the cylindrical first part and whose other end forms said second opening (15).

5. An apparatus according to claim 1, wherein the means (H) for applying a first acoustic signal to the liquid-empty part of the measuring container (1), the means (M) for recording a second acoustic signal generated in the measuring container (1) in response to the first signal, and the means (45) for determining a current amount of liquid in the measuring container (1) on the basis of the second acoustic signal are mounted in a measuring housing (4), the top wall of the measuring container (1) further comprises a sheet (12) for transferring acoustic signals, and
    wherein the measuring housing (4) is adapted to be secured in engagement with said sheet (12) to transfer said acoustic signals.

6. An apparatus according to claim 1, wherein the measuring container (1) further comprises a gas-filled resonator pipe (30) having a first opening (32/34) and a second opening (36), said pipe (30) being arranged to be in thermal connection with the liquid in the measuring container (1),
    means (M₂) are arranged to record a third acoustic signal generated in the temperature correcting pipe (30),
    the first opening (32/34) being arranged to be in acoustic connection with the means (H) for emitting fan acoustic signal so that the pipe (30) may be excited for resonance, the second opening (36) being arranged so as to communicate with the means (M₂).

7. An apparatus according to claim 6, wherein the first opening (32) is arranged so as to communicate with the measuring container part empty of liquid at any time, and the temperature resonator pipe correcting pipe (30) further comprises a cylindrical first part extending substantially vertically in the correctly mounted position and arranged in the measuring container (1) to extend upwards from the bottom wall (20) of the container, and a substantially cylindrical lateral branch whose one end terminates in the cylindrical first part and whose other end forms said opening (32).

8. A method of measuring the discharge of a liquid, in particular urine, from a patient using an apparatus comprising:
    a measuring container (1) which has a bottom wall (20), a top wall (25), side walls (22, 23) and an inlet opening for the liquid and which is adapted to define a state of maximum filling in which a liquid-empty part of the container (1) has a smallest volume,
    means (H) for emitting a first acoustic signal through the liquid-empty part of the measuring container (1),
    means (M) for recording a second acoustic signal generated in the liquid-empty part of the measuring container (1) in response to the first acoustic signal emitted through the liquid-empty part of the measuring container (1),
    data processing electronics (45) for determining a current amount of liquid in the measuring container (1) on the basis of the second acoustic signal, and
    a collecting container (11) which is in flow communication with the measuring container (1) via activatable connecting means, and which has a larger volume relative to the measuring container, said connecting means, being adapted to allow draining of the measuring container (1) in the state of maximum filling,
    wherein first data is determined by the data processing electronics for the change $A_{top}$ of the liquid amount in the container immediately after the draining,
    second data is determined by the data processing electronics (45) for the change $B_{bottom}$ of the liquid amount in the container immediately after the draining,
    wherein the first and the second sets of data are used for determining, by the data processing electronics, an estimate V of the discharge of liquid from the patient to the measuring container during the draining.

9. A method according to claim 8, wherein the estimate V is determined as $V=(T*A_{top}+T*B_{bottom})/2$, where T represents the duration of the draining.

10. A method according to claim 8, wherein the measuring container (1) has a measuring pipe (5), the method comprising a first opening (14), a second opening (15) and a third opening (16), wherein said first opening (14) being arranged to allow flow of the liquid into the measuring pipe (5) to define a liquid surface (7) in the measuring pipe (5), said second opening (15) being arranged so as to communicate with the part of the measuring container (1) empty of liquid at any time, said third opening (16) being arranged so as to communicate with the means (M) for recording the second acoustic signal, said second (15) and third (16) openings together with the surface (7) of the liquid in the measuring pipe (5) defining a liquid-empty resonance chamber to generate the second acoustic signal.

11. A method according to claim 8, wherein the connecting means further comprise an automatically operating syphon mechanism (9, 10).

12. A measuring container for use in connection with an apparatus as defined in claim 1, said measuring container (1) comprising:

a bottom wall (20) a top wall (25) and side walls (22, 23),
an inlet opening (2) for liquid,
an outlet opening for liquid,
a measuring pipe (5),
wherein one of the walls (20, 22, 23, 25) of the measuring container (1) comprises a preferably thin-walled sheet (12) adapted to transfer acoustic signals.

13. A measuring container according to claim 12, wherein the measuring pipe (5 further comprises a cylindrical first part extending substantially vertically in the correctly mounted position and arranged in the measuring container (1) to extend up from the bottom wall (20) of the container and terminating in openings (14, 16), and a substantially cylindrical lateral branch (6) whose one end terminates in the cylindrical first part and whose other end terminates in an opening (15).

14. A measuring container according to claim 13, further comprising an automatically operating syphon mechanism (9, 10) adapted to cause draining of the measuring container (1) in a state of maximum filling.

\* \* \* \* \*

UNITED STATES PATENT AND TRADEMARK OFFICE
CERTIFICATE OF CORRECTION

PATENT NO.    : 6,582,379 B1
DATED         : June 24, 2003
INVENTOR(S)   : Børge Stisen It is certified that error appears in the above-identified patent and that said Letters Patent is hereby corrected as shown below:

<u>Column 8,</u>
Line 62, delete "after" and substitute -- before -- in its place.

Signed and Sealed this

Eighteenth Day of May, 2004

JON W. DUDAS
*Acting Director of the United States Patent and Trademark Office*